US012370321B2

(12) United States Patent
Schabbach et al.

(10) Patent No.: US 12,370,321 B2
(45) Date of Patent: Jul. 29, 2025

(54) AWAKENING ELECTRONICS IN AN INJECTION DEVICE

(71) Applicant: Sanofi, Paris (FR)

(72) Inventors: Michael Schabbach, Frankfurt am Main (DE); Johannes Alpers, Frankfurt am Main (DE); Ganesh Appusamy Vedhachalam, Frankfurt am Main (DE); Jörg Bigalke, Frankfurt am Main (DE); Martin Rausch, Frankfurt am Main (DE); Anna Baccaro, Frankfurt am Main (DE)

(73) Assignee: Sanofi, Paris (FR)

( * ) Notice: Subject to any disclaimer, the term of this patent is extended or adjusted under 35 U.S.C. 154(b) by 847 days.

(21) Appl. No.: 17/622,385

(22) PCT Filed: Jun. 25, 2020

(86) PCT No.: PCT/EP2020/067851
§ 371 (c)(1),
(2) Date: Dec. 23, 2021

(87) PCT Pub. No.: WO2021/001254
PCT Pub. Date: Jan. 7, 2021

(65) Prior Publication Data
US 2022/0257870 A1 Aug. 18, 2022

(30) Foreign Application Priority Data

Jul. 1, 2019 (EP) .................................... 19305890

(51) Int. Cl.
*A61M 5/315* (2006.01)
*A61M 5/32* (2006.01)
(Continued)

(52) U.S. Cl.
CPC ...... *A61M 5/31568* (2013.01); *A61M 5/3155* (2013.01); *A61M 5/3202* (2013.01);
(Continued)

(58) Field of Classification Search
CPC ............ A61M 5/31568; A61M 5/3155; A61M 5/3202; A61M 5/20; A61M 2205/3317;
(Continued)

(56) References Cited

U.S. PATENT DOCUMENTS

| 5,769,877 A | 6/1998 | Barreras |
| 8,188,851 B2 | 5/2012 | Haartsen |

(Continued)

FOREIGN PATENT DOCUMENTS

| CN | 101522238 A | 9/2009 |
| CN | 101862489 A | 10/2010 |

(Continued)

OTHER PUBLICATIONS

International Preliminary Report on Patentability in International Appln. No. PCT/EP2018/080901, mailed on May 19, 2020, 12 pages.

(Continued)

*Primary Examiner* — Tasnim Mehjabin Ahmed
(74) *Attorney, Agent, or Firm* — Fish & Richardson P.C.

(57) ABSTRACT

An injection device comprising: an energy source configured to power an electronic system of the injection device; one or more sensors in communication with the energy source, the one or more sensors configured to cause an activation signal to be provided to the energy source to cause the energy source to enter a powered state from a sleep state; and a processor configured to facilitate one or more functions of the injection device when the injection device is in the powered state.

19 Claims, 5 Drawing Sheets

(51) Int. Cl.
*G16H 20/17* (2018.01)
*G16H 40/67* (2018.01)

(52) U.S. Cl.
CPC ............ *G16H 20/17* (2018.01); *G16H 40/67* (2018.01); *A61M 2205/3317* (2013.01); *A61M 2205/3327* (2013.01); *A61M 2205/3368* (2013.01); *A61M 2205/3375* (2013.01); *A61M 2205/8212* (2013.01)

(58) Field of Classification Search
CPC .. A61M 2205/3327; A61M 2205/3375; A61M 2205/8212; G16H 40/67
See application file for complete search history.

(56) References Cited

U.S. PATENT DOCUMENTS

| | | | |
|---|---|---|---|
| 8,712,483 | B2 | 4/2014 | Haartsen et al. |
| 9,108,006 | B2 | 8/2015 | Jensen et al. |
| 9,186,465 | B2 | 11/2015 | Jorgensen et al. |
| 9,289,559 | B2 | 3/2016 | Pedersen et al. |
| 9,459,089 | B2 | 10/2016 | Ganton et al. |
| 9,649,448 | B2 | 5/2017 | Madsen |
| 9,724,475 | B2 | 8/2017 | Krulevitch et al. |
| 11,771,832 | B2 | 10/2023 | Hammen et al. |
| 2002/0188419 | A1 | 12/2002 | Slate et al. |
| 2008/0129486 | A1 | 6/2008 | Jeckelmann et al. |
| 2011/0009821 | A1 | 1/2011 | Jespersen et al. |
| 2011/0025311 | A1 | 2/2011 | Chauvin et al. |
| 2011/0313350 | A1 | 12/2011 | Krulevitch et al. |
| 2012/0203178 | A1 | 8/2012 | Tverskoy |
| 2012/0268741 | A1 | 10/2012 | Pommereau et al. |
| 2015/0045729 | A1 | 2/2015 | Denzer et al. |
| 2015/0202376 | A1 | 7/2015 | Haupt |
| 2015/0241393 | A1 | 8/2015 | Ganti et al. |
| 2015/0292856 | A1 | 10/2015 | Ganton et al. |
| 2015/0320934 | A1 | 11/2015 | Draper et al. |
| 2016/0018900 | A1 | 1/2016 | Tu et al. |
| 2016/0066911 | A1 | 3/2016 | Baber et al. |
| 2016/0259913 | A1 | 9/2016 | Yu et al. |
| 2017/0281877 | A1 | 10/2017 | Marlin et al. |
| 2017/0312430 | A1* | 11/2017 | Schleicher ............ G01F 23/296 |
| 2017/0312455 | A1 | 11/2017 | Mirov et al. |
| 2018/0165422 | A1 | 6/2018 | Mirov |
| 2018/0200452 | A1 | 7/2018 | Marcoz et al. |
| 2018/0207366 | A1 | 7/2018 | Marcoz et al. |
| 2018/0353682 | A1 | 12/2018 | Laurence et al. |
| 2021/0038825 | A1 | 2/2021 | Marcoz et al. |
| 2021/0069421 | A1 | 3/2021 | Hammen et al. |
| 2021/0330892 | A1 | 10/2021 | Aldon et al. |
| 2022/0088312 | A1 | 3/2022 | Marcoz et al. |
| 2022/0088317 | A1 | 3/2022 | Marcoz et al. |
| 2023/0330348 | A1 | 10/2023 | Marcoz |
| 2023/0347066 | A1 | 11/2023 | Marcoz |
| 2023/0364346 | A1 | 11/2023 | Hammen et al. |
| 2023/0405233 | A1 | 12/2023 | Marcoz |
| 2024/0374831 | A1 | 11/2024 | Hammen et al. |

FOREIGN PATENT DOCUMENTS

| | | |
|---|---|---|
| CN | 102413855 A | 4/2012 |
| CN | 103648561 A | 3/2014 |
| CN | 104540535 A | 4/2015 |
| EP | 2923652 | 9/2015 |
| JP | 2007-510469 A | 4/2007 |
| JP | 2008-513077 A | 5/2008 |
| JP | 2012-519028 A | 8/2012 |
| JP | 2013-512060 A | 4/2013 |
| JP | 2015-505682 A | 2/2015 |
| JP | 2016-529016 A | 9/2016 |
| JP | 2017-520298 A | 7/2017 |
| JP | 2017-524399 A | 8/2017 |
| WO | WO 2005/046559 A2 | 5/2005 |
| WO | WO 2006/030194 A1 | 3/2006 |
| WO | WO 2008/045203 A1 | 4/2008 |
| WO | WO 2010/098927 A1 | 9/2010 |
| WO | WO 2010/098931 A1 | 9/2010 |
| WO | WO 2011/067187 A1 | 6/2011 |
| WO | WO 2012/160163 A1 | 11/2012 |
| WO | WO 2013/072444 A1 | 5/2013 |
| WO | WO 2014/029683 A1 | 2/2014 |
| WO | WO 2014/064691 | 5/2014 |
| WO | WO 2015/032715 A1 | 3/2015 |
| WO | WO 2015/187793 A1 | 12/2015 |
| WO | WO 2017/013463 A1 | 1/2017 |
| WO | WO 2017/013464 A1 | 1/2017 |
| WO | WO 2017/050781 A1 | 3/2017 |
| WO | WO 2017/155672 A1 | 9/2017 |
| WO | WO 2018/041798 | 3/2018 |
| WO | WO 2018/104289 A1 | 6/2018 |
| WO | WO 2018/138542 A1 | 8/2018 |
| WO | WO 2019/096726 | 5/2019 |
| WO | WO 2019/121608 | 6/2019 |
| WO | WO 2019/175790 A1 | 9/2019 |
| WO | WO 2020/217076 A1 | 10/2020 |
| WO | WO 2020/217094 A1 | 10/2020 |
| WO | WO 2021/220024 A1 | 11/2021 |
| WO | WO 2021/260404 A1 | 12/2021 |
| WO | WO 2022/079462 A1 | 4/2022 |

OTHER PUBLICATIONS

International Search Report and Written Opinion in International Appln. No. PCT/EP2018/080901, mailed on Jun. 4, 2019, 18 pages.
Levido, "Ferroelectric RAM," Oct. 28, 2020, retrieved on Oct. 6, 2022, retrieved from URL <https://circuitcellar.com/resources/ferroelectric-ram/>, 4 pages.
U.S. Appl. No. 16/763,380, filed May 12, 2020, Dietmar Hammen.
U.S. Appl. No. 18/357,445, filed Jul. 24, 2023, Dietmar Hammen.
U.S. Appl. No. 18/783,719, filed Jul. 25, 2024, Dietmar Hammen.
Davies, "Chapter 1: Rubber Transmission Spectra," The Rapra Collection of Infrared Spectra of Rubbers, Plastics and Thermoplastic Elastomers, Third Edition, 2007, retrieved on Jan. 26, 2022, retrieved from URL <"https://www.globalspec.com/reference/50757/203279/chapter-1-rubber-transmission-spectra">, 5 pages.
embedded.com [online], "Waking up a capacitive touch-sensing device with an MCU peripheral," Jul. 27, 2011, retrieved on Jan. 26, 2022, retrieved from URL <"https://www.embedded.com/waking-up-a-capacitive-touch-sensing-device-with-an-mcu-peripheral/">, 14 pages.
International Preliminary Report on Patentability in International Appln. No. PCT/EP2020/067851, dated Jan. 13, 2022, 7 pages.
International Search Report and Written Opinion in International Appln. No. PCT/EP2020/067851, dated Oct. 5, 2020, 9 pages.
signalquest.com [online], "SQ-SEN-200: Tilt & Vibration Sensor, Ultra Low Power, Omnidirectional," 1999-2022, retrieved on Jan. 27, 2022, retrieved from URL <"https://signalquest.com/product/components/sq-sen-200/">, 4 pages.
Third Party Observations in European Appln. No. 20735146.1, dated Jun. 30, 2023, 5 pages.

* cited by examiner

AWAKENING ELECTRONICS IN AN INJECTION DEVICE

CROSS REFERENCE TO RELATED APPLICATIONS

The present application is the national stage entry of International Patent Application No. PCT/EP2020/067851, filed on Jun. 25, 2020, and claims priority to Application No. EP 19305890.6, filed on Jul. 1, 2019, the disclosures of which are incorporated herein by reference.

TECHNICAL FIELD

This disclosure is directed to awakening electronics, and more particularly, to awakening electronics in an injection device.

BACKGROUND

Electronically-enabled injection devices assist users in safely administering a medicament and can also enable transmission of treatment data to the medical staff. Electronically enabled injection devices include an electronic component configured to provide continuous active sensing and connectivity properties, functions that require an energy supply. The energy supply can be a battery, which supplies power to the electric component. The configuration of electronically enabled injection devices can limit the capacity of the energy supply, which affects the life of the energy supply.

The life of an electronically enabled injection device can be limited by the life of its energy supply. Some electronically enabled injection devices can be kept on shelves for extended periods of time before being used. Current configurations of electronically enabled injection devices lead to idle drainage of the energy supply, such that, even if the electronically enabled injection device has not been used, long shelf life can exhaust the life of the energy supply. A low battery condition can lead to no- or malfunction of the device, an incorrect dosage, it can lead to a missed dosage, or it can even make the electronically enabled injection device unusable by stopping the operation of the electronic components.

SUMMARY

Implementations of the present disclosure include coupling mechanisms and systems configured for extending the life of electronically enabled injection devices by preventing idle drainage of the energy source. In accordance with one aspect of the present disclosure, an injection device includes an energy source configured to power an electronic system of the injection device, one or more sensors in communication with the energy source, the one or more sensors configured to cause an activation signal to be provided to the energy source to cause the energy source to enter a powered state from a sleep state, and a processor configured to facilitate one or more functions of the injection device when the injection device is in the powered state. Implementations can include one or more of the following features. In some implementations, the one or more functions include causing a medicament to be dispensed, determining an amount of medicament in the injection device, determining an amount of medicament dispensed by the injection device, or communicating with an external device.

In some implementations, the injection device further includes a cap that includes a magnet. The one or more sensor is a magnetic sensor, and the activation signal is provided in response to a magnetic field strength measured by the one or more sensor falling below a predetermined threshold. In some implementations, the magnetic sensor is a Reed switch or a Hall-effect sensor. The magnet is positioned proximate to the one or more sensor when the cap is attached to the injection device.

In some implementations, the injection device further includes a cap that includes a static element. The one or more sensor includes an electrode. The static element and the electrode are configured to be in contact when the cap is attached to the injection device. The static element is configured to create a static discharge when the static element rubs against a portion of the injection device, and the electrode is configured to detect the static discharge and cause the activation signal to be provided to the energy source in response.

In some implementations, the one or more sensor includes a motion sensor. The motion sensor is configured to detect a particular motion of the injection device and cause the activation signal to be provided to the energy source in response. The particular motion is a rotation of the injection device.

In some implementations, the one or more sensor includes a vibration sensor. The vibration sensor is configured to detect a particular sound or vibration of the injection device and cause the activation signal to be provided to the energy source in response. The particular sound or vibration occurs during dialing of a dose of medicament to be injected by the injection device.

In some implementations, the injection device is provided in temperature-resistant packaging that includes a temperature sensor that is configured to cause the activation signal to be provided to the energy source when the packaging is opened and the temperature sensor measures a temperature that satisfies a predetermined threshold.

It is appreciated that systems in accordance with the present disclosure can include any combination of the aspects and features described herein. That is to say that methods in accordance with the present disclosure are not limited to the combinations of aspects and features specifically described herein, but also include any combination of the aspects and features provided.

The details of one or more embodiments of the present disclosure are set forth in the accompanying drawings and the description below. Other features and advantages of the present disclosure will be apparent from the description and drawings, and from the claims.

BRIEF DESCRIPTION OF THE FIGURES

Like reference symbols in the various drawings indicate like elements.

DETAILED DESCRIPTION

Implementations of the present disclosure are generally directed to controlled activation of an energy source of an injection device to prevent idle drainage of the energy source. More particularly, implementations of the present disclosure are directed to a mechanism configured to receive a trigger signal and in response to receiving the trigger signal, generating an instantiation signal to activate the energy source of the injection device to the electronic component.

In some injection devices, the energy source of the injection device can be activated in response to false trigger signals, prior to intended usage of the injection device, leading to idle drainage of the energy source. Accordingly, use of electronic injection devices can be hindered by idle drainage of the energy source. In some injection devices, the activation process of the energy source of the injection device can take extended periods of time after the injection device is primed. Prolonged activation processes can render the injection devices as being unpractical. As described in further detail herein, implementations of the present disclosure address these challenges. For example, in accordance with implementations, the electronic injection device can be quickly (e.g., within seconds) activated in response to signals generated by reactants that are separated from each other until a trigger signal is initiated (e.g., during a priming step of a medicament administration) to prevent idle drainage of the energy source.

Figure 1:
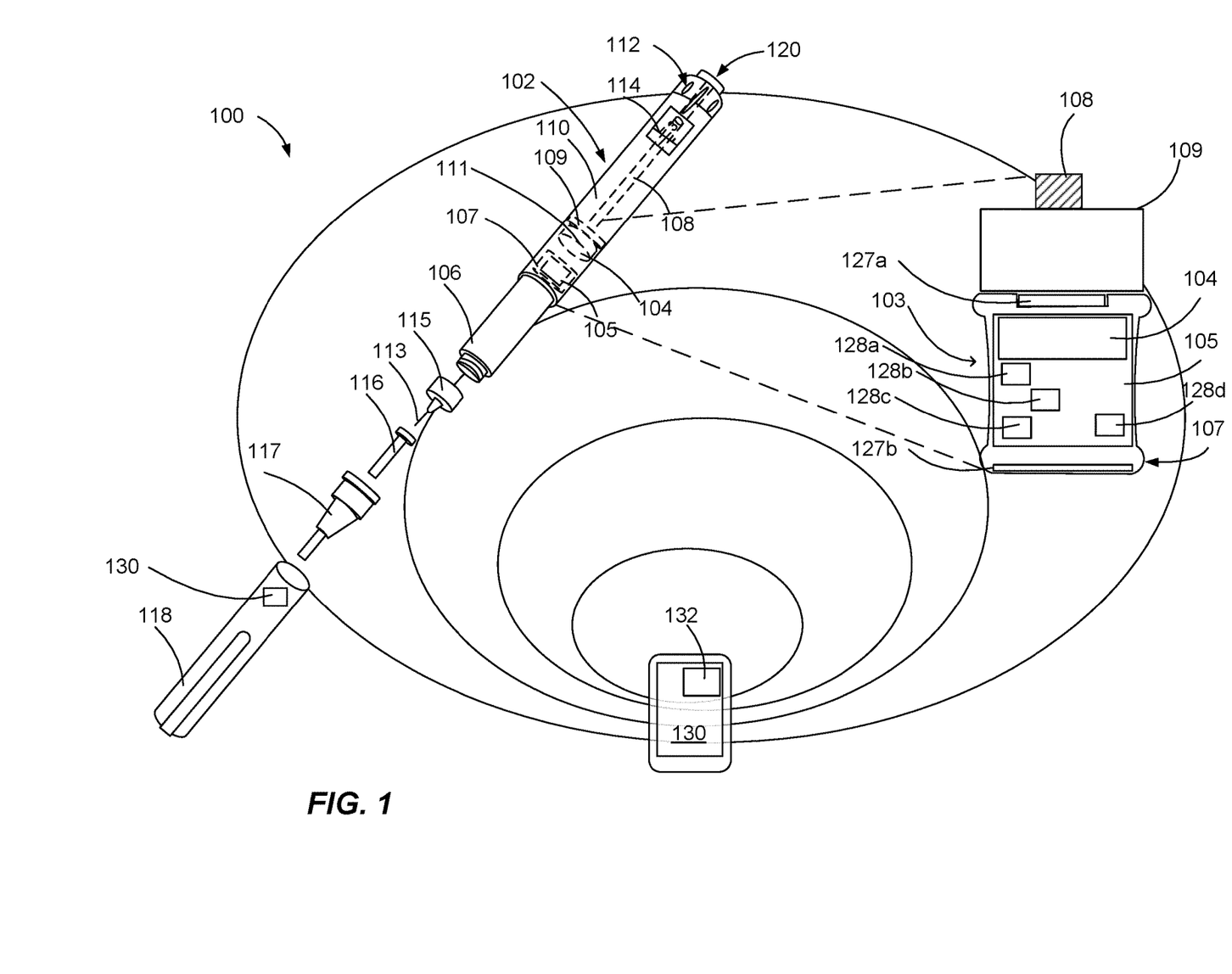
FIGS. 1-3 are exploded views of examples of devices in accordance with the present disclosure.
Figure 2:
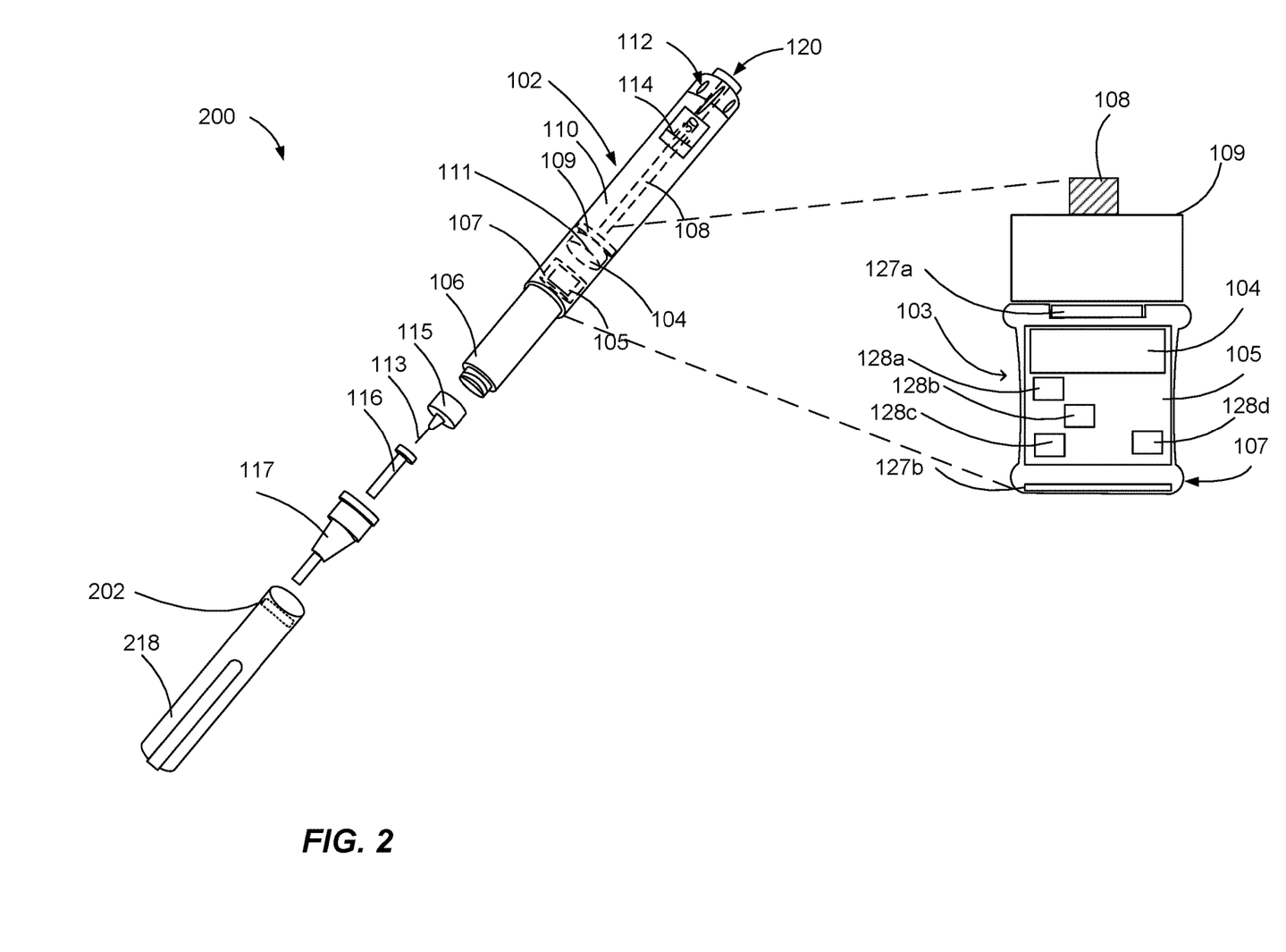
Figure 3:
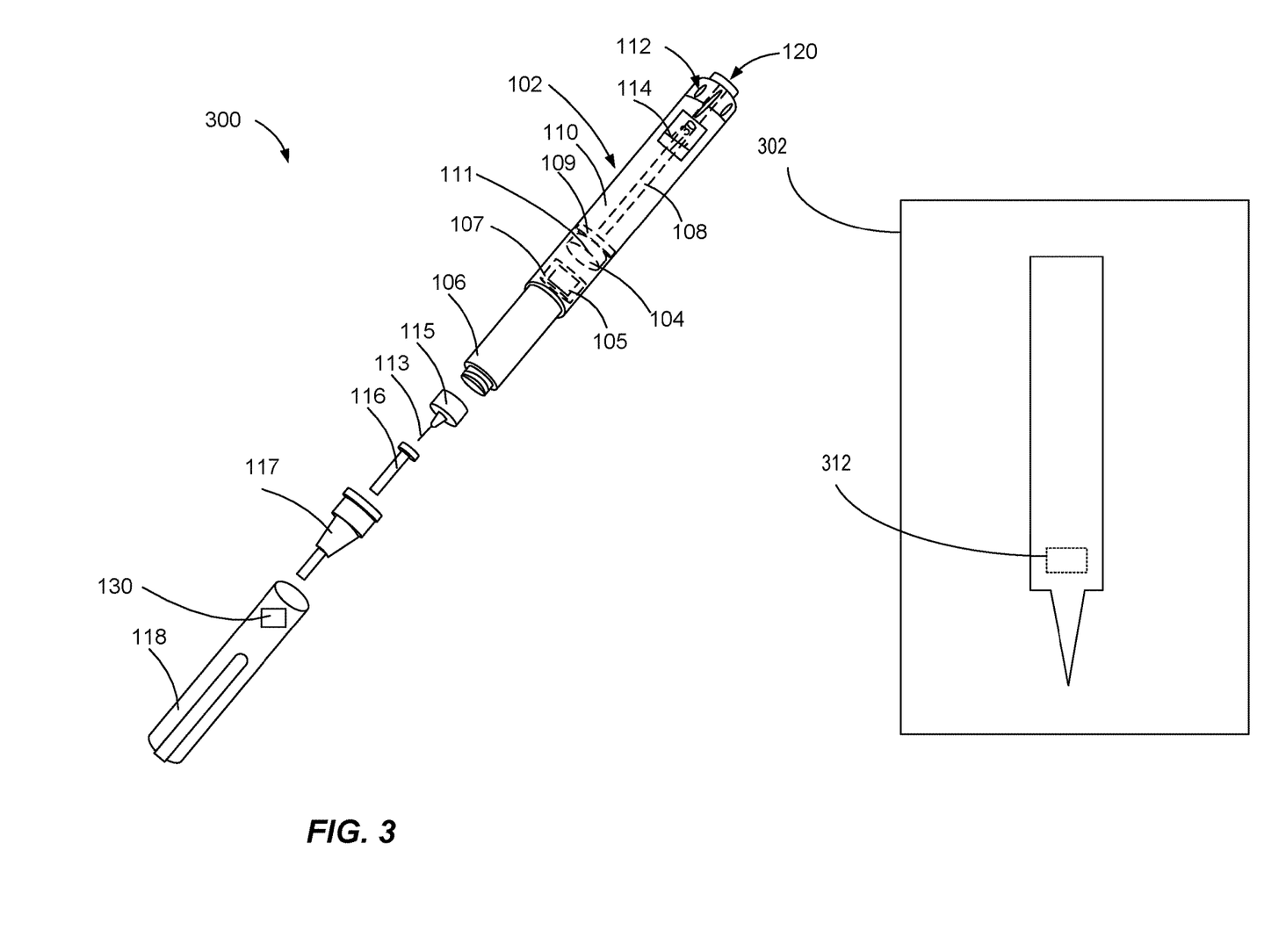

FIGS. 1-3 illustrate exploded views of example fluid delivery systems 100, 200, 300. Referring in particular to FIG. 1, the example fluid delivery system 100 can be configured to assist a user in injecting a fluid (e.g., a medicament) and facilitate sharing of medical data. The example fluid delivery systems 100 can include an injection device 102 and an external device 130. The injection device 102 can be an electronically enabled injection device configured to prevent idle drainage of an energy source 104. The injection device 102 can be a pre-filled, disposable injection pen or the injection device 102 can be a reusable injection pen with replaceable medicament reservoirs 106. The injection device 102 can be configured to communicate with the external device 130. The injection device 102 can transmit to the external device 130 operational data (e.g., data related to time of start of usage of injection device 102, temperature of injection device 102 during use and storage, etc.) and corresponding treatment data (e.g., amount of medicament dispensed, elapsed time for medicament to be dispensed by the injection device 102, etc.). In some implementations, the injection device 102 can be associated with an identifier that is used by the external device 130 to uniquely identify the injection device 102.

The injection device 102 can include a housing 110 and a needle assembly 115. The housing 110 can contain the energy source 104, an electronic system 105, a medicament reservoir 106, a stopper 107, a plunger rod 108, a plunger head 109, a priming component (e.g., dosage knob) 112, a dosage window 114, and an injection button 120. The housing 110 can be molded from a medical grade plastic material such as a liquid crystal polymer.

The medicament reservoir 106 can be configured to contain a fluid medicament. The medicament reservoir 106 can be a conventional, generally cylindrical, disposable container like a cartridge or a syringe used to package prepared fluids such as medicaments, anesthetics and the like. The medicament reservoir 106 can be provided with a pair of ends, one end having a pierceable membrane, which receives an inward end of needle 113 in sealing engagement. A dose of the contained medicament can be ejected from the injection device 102 by turning the dosage knob 112, and the selected dose is then displayed via dosage window 114, for instance in multiples of so-called International Units (IU), wherein one IU is the biological equivalent of about 45.5 micrograms of pure crystalline medicament (e.g., ½₂ mg). An example of a selected dose displayed in dosage window 114 may for instance be 30 IUs, as shown in FIG. 1. In some implementations, the selected dose can be displayed differently, for instance by an electronic display (e.g., the dosage window 114 may take the form of an electronic display). Turning the dosage knob 112 can cause a mechanical click sound to provide acoustical feedback to a user. The numbers displayed in dosage window 114 can be printed on a sleeve that is contained in housing 110 and mechanically interacts with a plunger head 109 that is fixed at the end of the plunger rod 108 and pushes the stopper 107 of the medicament reservoir 106.

The plunger head 109 (e.g., a back end of the plunger rod 108) can be configured to expel a portion of the fluid by displacing the stopper 107 contained within the medicament reservoir 106, such that a position of the stopper 107 is associated with an amount of the fluid within the injection device 102. The plunger rod 108 is mounted to the plunger head 109, which is mounted to the stopper 107.

The stopper 107 can be a flexible stopper, such as a rubber stopper or a rigid stopper with a sealing component. The stopper 107 can have an outwardly projecting rim matching the geometry and dimensions of the energy source 104. The stopper 107 can be of a sufficient length so that the stopper 107 is not ripped or twisted when being engaged by the plunger head 109. The stopper 107 can be of a sufficient volume to house a detection system 103, which can include the energy source 104 and the electronic system 105, among other components as described in more detail below.

The detection system 103 can include one or more sensors 127a, 127b. Similarly, the electronics system 105 (e.g., which can be part of the detection system 103) can include one or more sensors, such as a sensor 128b. The sensors 127a, 127b, 128b can be configured and arranged to detect a characteristic that causes the energy source 104 to become enabled. In other words, one or more of the sensors 127a, 127b, 128b may be configured to cause the injection device 102 to awaken (e.g., from a deep sleep state in which no or very little energy is being consumed by the injection device 102). Each of the sensors 127a, 127b, 128b may be configured to be powered (e.g., by very little power) such that they are operational enough to cause the wake-up signal to be provided. In some implementations, the energy source 104 itself can provide minimal power for allowing the sensors 127a, 127b, 128b enough power to operate sufficiently. In some implementations, the sensors 127a, 127b, 128b may have a separate power source, or may have their own power source.

The types of the one or more sensors 127a, 127b, 128b can be based on a particular mechanism employed for detecting a particular characteristic that indicates that the injection device 102 is to be awoken. For example, if a magnetic system is to be employed for causing the injection device 102 to awaken, one or more of the sensors 127a, 127b, 128b may be a magnetic sensor; if a light detection system is to be employed for causing the injection device 102 to awaken, one or more of the sensors 127a, 127b, 128b may be a photo sensor (e.g., a photodiode or a light dependent resistor); if multiple detection systems are to be employed, each of which can cause the injection device 102 to awaken, then multiple types of sensors may be provided.

Any combination of detection system functionality is possible. However, for illustrative purposes, implementations that include particular ones of the sensors 127a, 127b, 128*b* will be described with respect to particular systems and/or implementations, and each possible system for detecting a characteristic that causes the injection device 102 to awaken will be described in series separately. However, it should be understood that multiple systems may be incorporated into the detection system 103 for causing the injection device 102 to awaken in response to multiple different stimuli, and it should be understood that multiple sensors and/or different sensors can be employed for achieving the functionality described herein. For example, a particular wake-up technique may be described with respect to the sensor 128*b*, yet a similar wake-up technique could just as easily be implemented with the use of the sensor 127*a* and/or 127*b*.

The detection system 103 can be configured to generate an activation signal (e.g., a signal that causes the energy source 104 to awaken, power on, or increase power consumption from a sleep/deep sleep state to a powered-on state) based on signals provided by one or more of the sensors 127*a*, 127*b*, 128*b* and transmit the signal to the energy source 104 (e.g., directly or indirectly) to cause the electronic system 105 to be activated.

The energy source 104 can be a disposable or rechargeable battery, such as a 1.5V-5 V silver-oxide or lithium battery (e.g., SR626, SR516, SR416) or a super capacitor. In some implementations, energy source 104 can include a plurality of batteries (e.g., two 1.5V batteries). The energy source 104 can be configured to supply energy to the electronic system 105 under particular conditions, such as after receiving the activation signal from the detection system 103.

The electronic system 105 can include one or more electronic components configured to perform and/or assist with one or more functions of the injection device 102 (e.g., the ejection of the medicament) upon coupling with the energy source 104. For example, the electronic system 105 can include one or more processors 128*a*, the sensor 128*b* (e.g., as described above and in more detail below), an antenna 128*c*, and a motor 128*d*. The motor 128*d* can be configured to advance in micro-step increments to dispense a particular amount of medicament. In some implementations, the sensor 128*b* can provide, to the one or more processors 128*a*, a signal (e.g., a voltage), which is proportional to the amount of medicament dispensed or amount of medicament remaining in the medicament reservoir 106. Such functionality may be in addition to the "wake-up" functionality described in more detail herein. On the other hand, in some implementations, the electronics system 105 may include multiple sensors each configured to provide particular functionality (e.g., facilitating awakening of the energy source 104, facilitating other functionality of the injection device 102, etc.).

The one or more processors 128*a* can include a microprocessor. In some implementations, the microprocessor is a microcontroller, e.g., a combination of microprocessor components and other components formed in a single package. The microprocessor can be an arithmetic and/or a logic unit array. The one or more processors 128*a* can process one or more signals received from the other electronic components of the electronic system 105 (or the other sensors 127*a*, 127*b*) and transmit a signal to the antenna 128*c*. For example, the one or more processors 128*a* can be configured to execute operations on received data to generate output data. The one or more processors 128*a* can be configured to determine the amount of the fluid within the injection device 102 based at least in part on an electrical signal and transmit the data including information related to the amount of the fluid to the antenna 128*c* that can transmit it to the external device 130.

The antenna 128*c* can be a bluetooth or near-field communication (NFC) antenna. The antenna 128*c* can be configured to transmit signals to the one or more processors 128*a* and to the external device 130. The signals transmitted by the antenna 128*c* can include the amount of the fluid in the medicament reservoir 106, values measured by the sensor 128*b*, and the identifier of the injection device 102. A communication field 134 can be a bluetooth field or an NFC field, generated by the external device 130. The external device 130 can include a bluetooth or a RF module, a transmitter, a receiver, and an external processor 132. The external processor 132 can be configured to process the data transmitted by the injection device 102. The external device 130 can be configured to display (e.g., through a graphical user interface) the data received from the injection device 102 and processed by the external processor 132.

The needle assembly 115 includes a needle 113 that can be affixed to the housing 110. The needle 113 can be covered by an inner needle cap 116 and an outer needle cap 117, which in turn can be covered by a cap 118. When needle 113 is stuck into a skin portion of a patient, and then injection button 120 is pushed, the medicament dose displayed in dosage window 114 can be ejected from injection device 102. When the needle 113 of injection device 102 remains for a certain time in the skin portion after the injection button 120 is pushed, a high percentage (e.g., more than 90%) of the dose is actually injected into the patient's body. Ejection of the medicament dose can generate a mechanical click sound, which can be different from the sounds produced when using dosage knob 112.

The injection device 102 can be used for several injection processes until either medicament reservoir 106 is empty or the expiration date of injection device 102 (e.g., 28 days after the first use) is reached. Before using injection device 102 for the first time, it may be necessary to perform a priming operation to couple the energy source 104 to the electric component and/or to remove air from medicament reservoir 106 and needle 113. For instance, the priming operation can include selecting two units of medicament and pressing injection button 120 while holding injection device 102 with the needle 113 upwards. In some implementations, the impulse generated by selecting two units of medicament or pressing injection button 120 can trigger the electrical coupling of the energy source 104 with the electronic system 105 by mechanical means (e.g., a mechanical switch).

In some implementations, the electronic components of the electronic system 105 can be integrated within the housing 110 at a single location, or at multiple locations (e.g., within or attached to a plunger rod 108, and a cavity in the plunger head 109). In some implementations, one or more components of the electronic system 105 can be contained within the stopper 107. In some implementations, one or more components of the electronic system 105 can be contained within the plunger head 109.

In some implementations, the location of the energy source 104 and/or the location of one or more electronic components of the electronic system 105 can be selected independent from the coupling between the electronic system 105 and the energy source 104. In some implementations, one or more characteristics of one or more electronic components of the electronic system 105 and/or one or more characteristics of the energy source 104 can be selected to couple and/or uncouple the electronic system 105 from the energy source 104.

In some implementations, the housing 110 of the injection device 102 can be configured to be separated or broken in multiple segments to provide a user access to the energy source 104, to enable separate disposal of the energy source 104. In some implementations, the medicament reservoir 106 to be assembled with the injection device 102 is manufactured with inserted stopper 107, is filled with the fluid medicament, and is closed with a crimp seal.

During the manufacturing and storage of the medicament reservoir 106 prior to assembly with the injection device 102, the energy source 104 is not activated (or, e.g., is in a sleep or deep sleep state). By keeping the energy source 104 deactivated, no idle drainage of energy can occur during manufacturing and potential long storage of the medicament reservoir 106. In the subsequent step of device priming (or some other action, as described herein), the energy source 104 of the injection device 102 is activated (or, e.g., awoken) to power the electronic system 105. In some implementations, the energy source 104 can be connected to the electronic system 105 to enable controls of functionality of the injection device 102 upon receipt of an activation signal. In some implementations, the energy source 104 may be temporarily awoken during assembly to confirm proper operation of the injection device 102 and the electronics system 105. Connection to the energy source 104 as manufacturing step allows to wake-up the electronic system 105 and to generate feedback signals that confirm proper system functionality. After performing such in-process controls, the energy source 104 may be disconnected again, or the electronic system 105 may be set in sleep mode through appropriate software features that reduce energy consumption until a priming step is performed to wake up the electronic system 105 or some other action occurs.

In some implementations, one or more of the sensors 127a, 127b, 128b may be a magnetic sensor. For example, still referring to FIG. 1, the sensor 127b may be a magnetic sensor that is configured to sense magnetic fields and provide a signal that corresponds to the sensed magnetic fields. The magnetic sensor 127b is in communication with the energy source 104. Thus, the magnetic sensor 127b can provide an activation signal that causes the energy source 104 to awaken as described herein. For example, if a magnetic threshold is satisfied (e.g., if a sensed magnetic field strength falls below a threshold magnetic value), the magnetic sensor 127b can provide a signal that causes the activation signal to be generated. In some implementations, the magnetic sensor 127b includes one or both of a Reed switch or a Hall-effect sensor.

In an example implementation, a magnet 130 can be provided on/in the cap 118 of the injection device 102. The magnet 130 may be embedded in the cap 118 at a position such that the magnet 130 is proximate to the magnetic sensor 127b when the cap 118 is in a closed position (e.g., when the cap 118 largely covers the medicament reservoir 106. When the cap 118 is in the closed position, a magnetic field generated by the magnet 130 is sufficient to cause the magnetic sensor 127b to refrain from emitting an activation signal. In other words, when the cap 118 is closed over the injection device 102, a predetermined magnetic threshold is satisfied. When the cap 118 is removed from the injection device, the magnet 130 moves away from the magnetic sensor 127b such that the magnetic field sensed by the magnetic sensor 127b no longer satisfies the magnetic threshold, and in turn, the magnetic sensor 127b provides an activation signal to the energy source 104. The energy source 104, in turn, is instructed to awaken (e.g., due to electronics incorporated in the energy source 104 that are programmed to awaken in response to such an activation signal).

In some implementations, the magnet 130 and/or the magnetic sensor 127b may be positioned elsewhere. For example, the magnet 130 may be positioned at a location where a removable component of the injection device 102 resides. Such a removable component may be configured to be removed upon first use of the injection device 102. Therefore, the activation signal can be provided when the removable component is removed prior to first use of the injection device 102, thereby preventing the injection device 102 from awakening early (e.g., before energy consumption is required for use). In some implementations, the magnet 130 may be incorporated in the inner needle cap 116 and/or the outer needle cap 117, among other locations. In some implementations, the magnet may be positioned in packaging of the injection device 102. When the injection device 102 is removed from the packaging, the magnetic threshold may no longer be satisfied, and the magnetic sensor 127b may provide the activation signal.

In some implementations, removal of the cap 118 of the injection device 102 may cause the energy source 104 to awaken by other means (e.g., other than by receiving an activation signal from the magnetic sensor 127b). In some implementations, detection of a static discharge may cause the energy source 104 to awaken. FIG. 2 shows another example of a medicament injection system 200 in which the injection device 102 includes a cap 218 that includes a component for causing static discharge upon interaction with another component of the injection device 102. In particular, the cap 218 includes a static element 202 that is positioned around a periphery of the opening of the cap 218 on the inside surface. The static element 202 is configured to interface with one of the sensors, for example, the sensor 127a of the detection system 103. The sensor 127a may be or include an electrode. The sensor 127a may be suitable for such a purpose because, as shown in FIG. 1, the sensor 127a may be exposed through the stopper 107 (e.g., a surface of the electrode 127a can be exposed such that the electrode 127a can make contact with the static element 202). The static element 202 may include a metallic material that is configured to create a static discharge when it is rubbed against the electrode 127a. In some implementations, the static element 202 is configured to create a static discharge when it is rubbed against another portion of the injection device 102, and the electrode 127a is configured to detect such a static discharge. Similarly, in some implementations, the electrode 127a may include a material that is configured to create such a static discharge under the circumstances, and may also include functionality for causing an activation signal to be provided to the energy source 104 when a static discharge is detected. Such an activation signal may operate in a manner similar to the activation signal described above with respect to the magnetic sensor 127b. When the cap 218 is removed from its closed position, the static element 202 rubs against the electrode 127a and a static discharge is created. The electrode 127a then causes the energy source 104a to be instructed to awaken.

In some implementations, removal of the cap 118, 218 may also cause the energy source 104 to awaken by other means. For example, force/movement/acceleration required to remove the cap 118, 218 may trigger the awakening of the energy source 104. In some implementations, one of the sensors (e.g., the sensor 128b) may be a motion sensor 128b that includes one or more accelerometers and/or one or more gyroscopes. The motion sensor 128b is configured to operate in a very low power mode (e.g., a stand-by mode). The motion sensor 128b may be configured to detect the force that is inherently exerted upon removal of the cap 118, 218. For example, when the cap 118, 218 is removed, a tactile "click" is generated. Such a click can be detected by the motion sensor 128b, and the motion sensor 128b may provide the activation signal to the energy source 104.

In some implementations, the movements detected by the motion sensor 128b must sufficiently match a particular profile (e.g., a cap removal profile) in order for the motion sensor 128b to provide an activation signal to the energy source 104. Such a requirement can prevent the energy source 104 from inadvertently waking up during transport, shipping, and/or simple movements of the injection device 102. In some implementations, the profile for cap removal can be determined in advance (e.g., by testing, calibration, etc.). Movement profiles that match the "click" generated by cap removal can be identified, and in turn, the energy source 104 can be awoken in response.

In some implementations, the energy source 104 may be awoken in response to a particular characteristic movement of the injection device 102. That is, the wake-up can be triggered by a special movement which is performed by a patient when he or she is using the pen for the first time. In some examples, the movement can include unwrapping the injection device 102 from manufacturer's packaging, removing the injection device 102 from boxed packaging, priming the injection device 102, and/or dialing the injection device 102 to receive a particular dose of medicament, to name a few. Such movements of the injection device 102 can correspond to a particular motion profile, and when the injection device 102 performs such motions, the motion sensor 128b may cause the activation signal to be provided to the energy source 104. In some implementations, the particular movement is chosen such that the movement is not one that would occur prior to the intended activation of the injection device 102. For example, the particular movement may be complex enough that the injection device 102 would not be inadvertently awoken during shipping or unloading.

In some implementations, the particular movement may include rotation of the injection device 102. For example, the user may be instructed to rotate the injection device 360 degrees axially or 360 degrees along a length of the injection device. Such a motion may be one that is not susceptible to occurring during shipping of the injection device 102. The motion sensor 128b may detect such a motion and cause the activation signal to be provided to the energy source 104.

As described above, the sensors 127a, 127b, 128b may be configured to receive minimal power to allow the sensors 127a, 127b, 128b to sufficiently operate for detecting a wake-up event. However, such power is minimal and does not result in excessive power loss. While the power may come from the energy source 104 in its deep sleep state, in some implementations, the sensors 127a, 127b, 128b may have a separate power source, or may have their own power source.

In some implementations, the motion sensor may be positioned elsewhere for detecting removal of the cap 118, 218. For example, the motion sensor may be positioned on the housing 110 of the injection device 102, on the cap 118, 218, etc.

In some implementations, one of the sensors (e.g., the sensor 127a) may be an acoustic sensor (e.g., a microphone) that is configured to detect particular characteristic sounds that emanate from the injection device 102. For example, a specific noise generated by the priming or dialing process can be detected by the acoustic sensor 127a, and in response, the acoustic sensor 127a can cause an activation signal to be provided to the energy source 104. In some implementations, the "click" sound that occurs when a dose is dialed into the injection device 102 may have a particular signature that is detected by the acoustic sensor 127a. In some implementations, the acoustic sensor 127a may alternatively be a vibration sensor that is configured to detect vibrations that occur during dose dialing or priming, and the vibration sensor may cause the activation signal to be provided to the energy source 104 in response to detecting a matching vibration profile. In some implementations, the acoustic sensor 127a and/or the vibration sensor may be a MEMS based piezo element that is used to provide the minimal power required for the sensor to cause the activation signal to be generated.

In some implementations, one of the sensors (e.g., the sensor 127a) may be a light sensor such as a photodiode 127a. The sensors 127a may be suitable for the photodiode 127a because it may be exposed (e.g., a void or a window in the stopper 107 may allow light to pass to the photodiode 127a). Prior to use of the injection device 102, the injection device 102 is covered by the cap 118, 218. The cap 118, 218 prevents light from reaching the photodiode 127a. When the cap 118, 218 is removed, light will typically reach the photodiode 127a. If the light satisfies a threshold (e.g., a relatively low threshold because the photodiode 127a is typically otherwise is complete darkness), the photodiode 127a may provide a signal to the energy source 104 that causes the energy source 104 to awaken from its sleep state.

While the photodiode 127a has been described as receiving light directly (e.g., through a void or a window), in some implementations, the photodiode 127a may be embedded in the stopper 107, and the light may be such that its wavelength permits it to pass through the stopper 107 (e.g., made of rubber). In other words, the light may have characteristics such that it cannot pass through the cap 118, 218, but it can pass through the rubber stopper 107. In this way, the presence of the cap 118, 218 can prevent the energy source 104 from awakening, but removal of the cap 118, 218 and exposure of the light to the stopper 107 may result in the energy source 104 being awoken. In some implementations, the light may be especially designed for causing the injection device 102 to awaken. For example, the light may satisfy a rubber transmission spectra (e.g., in the infrared spectra), and a special device may be used to apply such light to the injection device 102.

As briefly described above, in some implementations, the injection device 102 may be provided with packaging that is configured to assist with the wake-up functionality of the energy source 104. FIG. 3 shows another example of a fluid delivery system 300 that includes the injection device 102 and packaging 302 that is configured to house the injection device 102. The packaging 302 may have a cut-out that is sized and shaped to accommodate the injection device 102 such that the injection device 102 can sit in the packaging 302 (e.g., snugly). The packaging 302 may include a wrapping (e.g., paper, plastic, etc.) that must be removed before the packaging 302 can be opened and the injection device 102 can be removed. In some implementations, the packaging 302 and/or the wrapping may be made of a material that is resistant to temperature changes. For example, the packaging 302 may cause the temperature within to remain below approximately 7° C. When the packaging 302 is closed and the wrapping is in place, the injection device 102 may remain at a temperature below 7° C. The use of sufficient insulation in the packaging 302 may prevent the device from inadvertently rising above 7° C. during transport and before its first intended use.

The packaging 302 may include a temperature sensor 312 that is configured to sense the temperature within the packaging 302 and ensure that the injection device 102 is maintained at a temperature below 7° C. If the temperature rises above 7° C. (e.g., when the packaging 302 is opened and the injection device 102 is removed from the packaging 302), the injection device 102 may be configured to awaken (e.g., the temperature sensor 312 may be configured to cause an activation signal to be provided to the energy source 104, thereby causing the injection device 102 to wake from its sleep state). In some implementations, the temperature sensor 302 may be configured to wirelessly communicate with the injection device 102 for allowing the temperature sensor 302 to instruct the activation signal to be generated. In some implementations, the temperature sensor 302 may be incorporated into the injection device 102 itself (e.g. as one of the sensors 127a, 127b, 128b). In this way, the temperature sensor 302 need not emit a signal to the energy source 104, but rather the sensor 127a, 127b, 128b can simply provide a direct signal (e.g., over a wired connection) to cause the energy source to receive the activation signal.

While various possible techniques for causing the injection device 102 to awaken have been described, others are also possible. In some implementations, the injection device may be provided with a docking station that is configured to allow the injection device to mount in an upright position. Placing the injection device 102 in the mounting station for the first time can cause an activation signal to be provided to the energy source 104. In some implementations, the docking station may also be equipped with connectivity to the injection device 102 detection system 103 and/or electronics system 105 as well as to a WiFi network in a household. In some implementations, capacitive means, NFC, magnetic switches or other technologies could be implemented to cause the energy source 104 to awaken, and such interaction could be easily implemented because two devices are permitted to interact.

In some implementations, a pull tab may be positioned proximate to the energy source 104 such that power is prevented from fully flowing through the injection device 102 while the pull tab is in place. Prior to first use, the user could remove the pull tab, thereby causing the injection device to awake from its sleep state and achieve full functionality.

In some implementations, a manual switch may be provided on the injection device 102. Prior to first use, the user can press/flip the switch, thereby causing the activation signal to be provided to the energy source 104 and causing the device to awaken from its sleep state. In some implementations, the switch may be a touch button (e.g., a capacitive touch button).

In some implementations, a separate device (e.g., the external device 130 of FIG. 1) may be used to cause the energy source 104 to awaken from its sleep state. For example, the external device 130 may be a smart phone or a tablet that the patient can interact with to cause the injection device 102 to awaken. The external device can communicate with the injection device via the antenna 128c (e.g., over a short-range wireless protocol such as WiFi, NFC, RFID, etc.). In particular, the external device 130 may form a connection with the injection device 102, the user can interact with the external device 130 to instruct the external device 130 to cause the injection device to awaken, the external device 130 can provide an activation signal to the injection device 102, and the user can then use the injection device for the first time.

Figure 4:
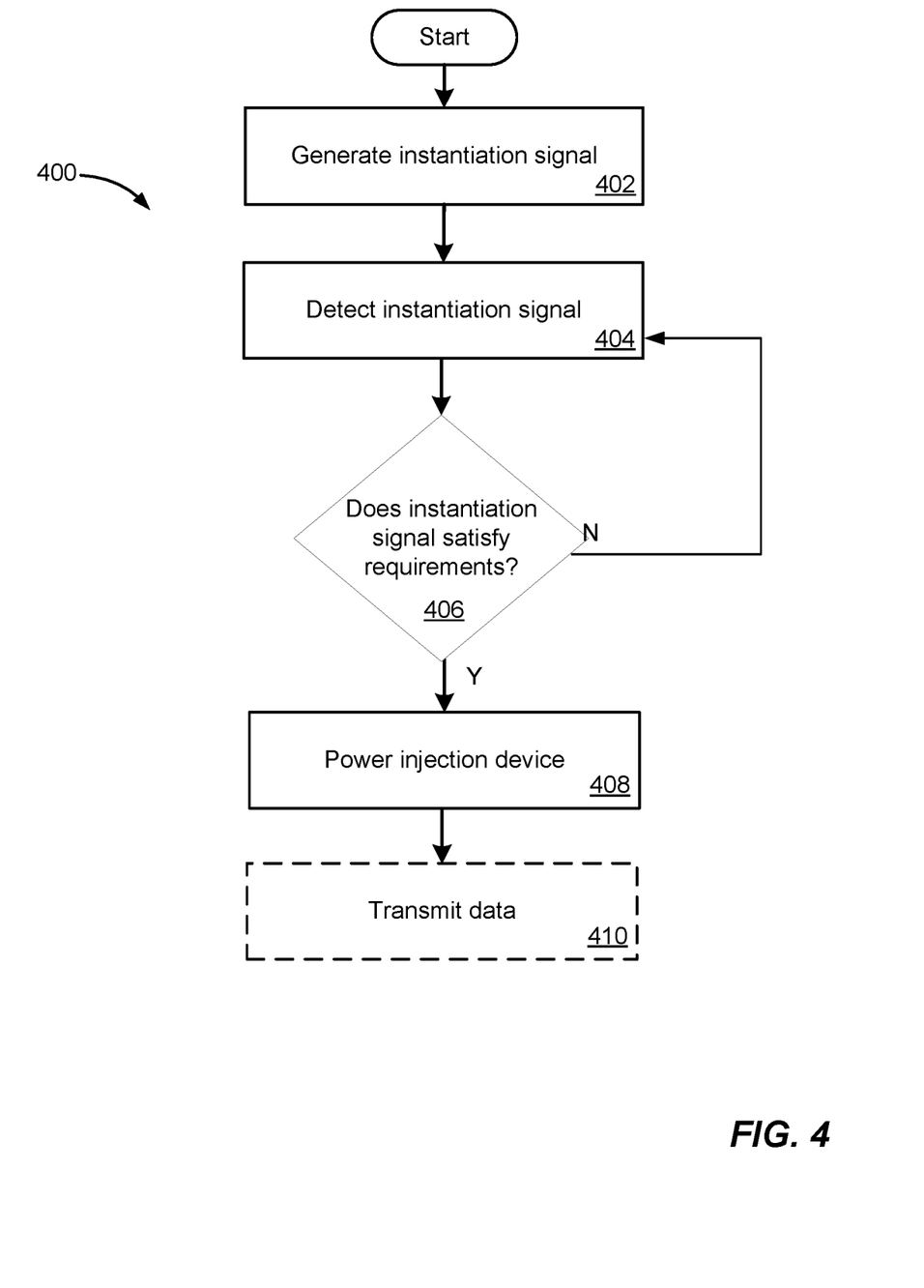
FIG. 4 is a flowchart illustrating an example process that can be executed to perform operations of the present disclosure.

FIG. 4 is a flowchart illustrating an example process 400 that can be executed by devices and systems described with reference to FIGS. 1-3. An instantiation signal is generated by one or more of the techniques described herein (402). Using the magnetic implementations as an example, the cap with the magnet is removed, and the magnetic field sensed by the magnetic sensor drops below the predetermined threshold. Using the light-induced wake-up example, the cap may be removed from the injection device, and the photodiode may be exposed to light. Using the electrostatic discharge example, the cap can be removed from the injection device, and the electrode may sense the electrostatic discharge (e.g., caused in part by the electrode). Using the motion sensor cap removal detection example, the signature of the cap being removed from the injection device may match a predetermined signature indicative of cap removal.

The instantiation signal is detected by a detection system including one or more sensors (404). In some implementations, the detection of the instantiation signal can include determining a difference between the measurements of two sensors. In some implementations, multiple measurements by multiple sensors in combination may be detected.

A determination is made as to whether the instantiation signal satisfies one or more requirements (406). In some implementations, the instantiation signal (e.g., a measurement from one or more sensors) is compared to a threshold, which may or may not be satisfied. In some implementations, a signature (e.g., a reading from a motion sensor or a vibration sensor) is compared to a predetermined motion signature or sound/vibration signature. If the comparison indicates that the measurement satisfies the activation threshold or matches the particular signature, the process 400 proceeds to the next step (408). If the requirements are not satisfied, the process 400 reverts to the detection of instantiation signal (404) step and the process 400 awaits generation of another signal from the one or more sensors.

If the comparison indicates that the requirements are satisfied by the signal(s), an activation signal is generated, by the detection system, to cause the electronic system to be activated, and the injection device is powered (408) (or, e.g., awoken from a sleep or deep sleep state). In some implementations, the energy source can be coupled with the electronic component by a mechanism (e.g., gear mechanism). In some implementations, the mechanism can include one or more components (e.g., a plunger rod 108, a plunger head 109, as described with reference to FIGS. 1-3) configured to shift the energy source from one position, in which the energy source is electrically decoupled from the electronic component to a second position, in which the energy source is electrically coupled with the electronic component. In some implementations, the mechanism can include a switch (e.g., an electronic switch, a relay, a software switch, etc.) configured to be activated for electrically coupling the energy source to the electronic component.

Figure 5:
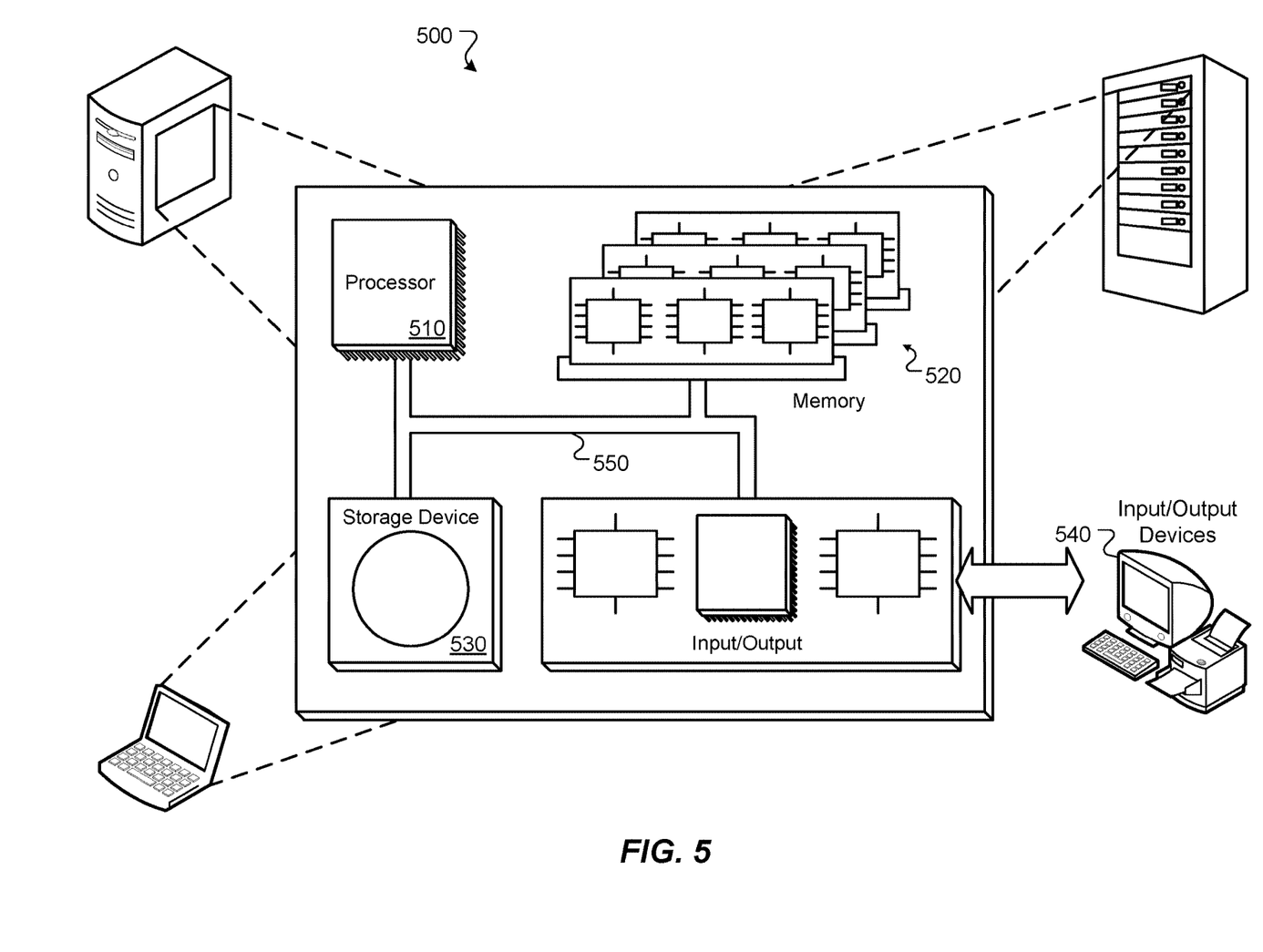
FIG. 5 is a schematic illustration of example computer systems that can be used to execute implementations of the present disclosure.

In response to coupling the energy source with the electronic component, an electric signal is optionally generated (410). The electric signal can be generated to assist and/or perform an operation of the injection device (e.g., control an administration of a medicament) and/or measure one or more parameters associated to the injection device (e.g., amount of a medicament, temperature, etc.). The electric signal can include generation of injection device data. The injection device data can include a unique identifier for the injection device, an amount of administered medicament, an amount of medicament within a cartridge and/or injection device, a medicament temperature, a timestamp of coupling the energy source to the electronic component, a location, and/or a situation specific data for the injection device. Such a step is optional in the sense that it need not occur immediately, but may be performed at a later time post-activation FIG. 5 shows a schematic diagram of an example computing system 500. The system 500 can be used for the operations described in association with the implementations described herein. For example, the system 500 may be included in any or all of the server components discussed herein. The system 500 includes a processor 510, a memory 520, a storage device 530, and an input/output device 540. Each of the components 510, 520, 530, and 540 are interconnected using a system bus 550. The processor 510 is capable of processing instructions for execution within the system 500. In one implementation, the processor 510 is a single-threaded processor. In another implementation, the processor 510 is a multi-threaded processor. The processor 510 is capable of processing instructions stored in the memory 520 or on the storage device 530 to display graphical information for a user interface on the input/output device 540.

The memory 520 stores information within the system 500. In one implementation, the memory 520 is a computer-readable medium. In one implementation, the memory 520 is a volatile memory unit. In another implementation, the memory 520 is a non-volatile memory unit. The storage device 530 is capable of providing mass storage for the system 500. In one implementation, the storage device 530 is a computer-readable medium. In various different implementations, the storage device 530 may be a floppy disk device, a hard disk device, an optical disk device, or a tape device. The input/output device 540 provides input/output operations for the system 500. In one implementation, the input/output device 540 includes a keyboard and/or pointing device. In another implementation, the input/output device 540 includes a display unit for displaying graphical user interfaces that enable a user to access data related to an item that is collected, stored and queried as described with reference to FIGS. 1-5.

The features described can be implemented in digital electronic circuitry, or in computer hardware, firmware, software, or in combinations of them. The apparatus can be implemented in a computer program product tangibly embodied in an information carrier, e.g., in a machine-readable storage device, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, e.g., a LAN, a WAN, and the computers and networks forming the Internet.

The computer system can include clients and servers. A client and server are generally remote from each other and typically interact through a network, such as the described one. The relationship of client and server arises by virtue of computer programs running on the respective computers and having a client-server relationship to each other.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −3° C. to about 3° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des (B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin; B29-N—(N-lithocholyl-gamma-glutamyl)-des (B30) human insulin; B29-N-(ω-carboxyheptadecanoyl)-des (B30) human insulin and B29-N-(ω-carboxyhepta-decanoyl) human insulin.

Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091 MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

A number of implementations of the present disclosure have been described. Nevertheless, it will be understood that various modifications may be made without departing from the spirit and scope of the present disclosure. Accordingly, other implementations are within the scope of the following claims.

The invention claimed is:

1. An injection device comprising:
   an energy source configured to power an electronic system of the injection device;
   one or more sensors in communication with the energy source, the one or more sensors being configured to cause an activation signal to be provided to the energy source to cause the energy source to enter a powered state from a sleep state; and
   a processor configured to facilitate one or more functions of the injection device when the energy source is in the powered state,
   wherein at least one of the one or more sensors is configured to emit the activation signal.

2. The injection device of claim 1, further comprising a cap that includes a magnet, wherein at least one of the one or more sensors is a magnetic sensor.

3. The injection device of claim 2, wherein the magnet is positioned proximate to the one or more sensors when the cap is attached to the injection device.

4. The injection device of claim 1, wherein at least one of the one or more sensors is configured to measure a magnetic field strength, and wherein the activation signal is provided in response to the magnetic field strength falling below a predetermined threshold.

5. The injection device of claim 1, wherein the one or more sensors includes a Reed switch or a Hall-effect sensor.

6. The injection device of claim 1, further comprising a cap that includes a static element, wherein at least one of the one or more sensors includes an electrode.

7. The injection device of claim 6, wherein the static element and the electrode are configured to be in contact with each other when the cap is attached to the injection device.

8. The injection device of claim 6, wherein the static element is configured to create a static discharge when the static element rubs against a portion of the injection device, and the electrode is configured to detect the static discharge and cause the activation signal to be provided to the energy source in response.

9. The injection device of claim 1, wherein at least one of the one or more sensors includes a motion sensor.

10. The injection device of claim 9, wherein the motion sensor is configured to detect a particular motion of the injection device and cause the activation signal to be provided to the energy source in response.

11. The injection device of claim 10, wherein the particular motion is a rotation of the injection device.

12. The injection device of claim 1, wherein at least one of the one or more sensors includes a vibration sensor.

13. The injection device of claim 12, wherein the vibration sensor is configured to detect a particular sound or vibration of the injection device and cause the activation signal to be provided to the energy source in response, the particular sound or vibration occurring during dialing of a dose of medicament to be injected by the injection device.

14. The injection device of claim 1, wherein the injection device is provided in a temperature-resistant packaging that includes a temperature sensor that is configured to cause the activation signal to be provided to the energy source when (i) the packaging is opened and (ii) the temperature sensor measures a temperature that satisfies a predetermined threshold.

15. The injection device of claim 1, wherein the one or more functions include at least one of causing a medicament to be dispensed, determining an amount of medicament in the injection device, determining an amount of medicament dispensed by the injection device, or communicating with an external device.

16. An injection device comprising:

a container containing medicament;

an energy source configured to power an electronic system of the injection device;

one or more sensors in communication with the energy source, the one or more sensors being configured to cause an activation signal to be provided to the energy source to cause the energy source to enter a powered state from a sleep state; and a processor configured to facilitate one or more functions of the injection device when the energy source is in the powered state, wherein at least one of the one or more sensors is configured to emit the activation signal, and wherein the one or more functions include at least one of causing the medicament to be dispensed, determining an amount of the medicament in the injection device, determining an amount of the medicament dispensed by the injection device, or communicating with an external device.

17. The injection device of claim 16, wherein the container is disposable.

18. The injection device of claim 16, further comprising a cap, wherein at least one sensor of the one or more sensors is configured detect a movement of the cap relative to the sensor, and in response, cause the activation signal to be provided to the energy source.

19. The injection device of claim 16, wherein the one or more sensors include at least one of a magnetic sensor configured to measure magnetic field strength within the injection device, an electrode configured to detect a static discharge within the injection device, a motion sensor, or a vibration sensor.

* * * * *